United States Patent

Wulff et al.

[11] Patent Number: 5,698,600
[45] Date of Patent: Dec. 16, 1997

[54] PROCESS FOR THE PRODUCTION OF BISPHENOLS WITH THE USE OF NEW COCATALYSTS

[75] Inventors: Claus Wulff, Krefeld; Gerhard Fennhoff, Willich; Alfred Eitel, Dormagen, all of Germany

[73] Assignee: Bayer AG, Leverkusen, Germany

[21] Appl. No.: 730,087

[22] Filed: Oct. 15, 1996

[30] Foreign Application Priority Data

Oct. 24, 1995 [DE] Germany .............. 195 39 444.5

[51] Int. Cl.[6] .................................. C07C 39/17
[52] U.S. Cl. ............... 521/32; 521/33; 568/196; 568/718; 568/721; 568/722; 568/723; 568/727; 568/728
[58] Field of Search ................. 568/721, 718, 568/722, 727, 196, 728, 723; 521/32, 33

[56] References Cited

U.S. PATENT DOCUMENTS

| 2,182,308 | 12/1939 | Britten | 260/619 |
|---|---|---|---|
| 2,191,831 | 2/1940 | Perkins | 260/619 |
| 2,468,982 | 5/1949 | Jansen | 269/619 |
| 2,623,908 | 12/1952 | Stoesser | 260/619 |
| 2,775,620 | 12/1956 | Williamson | 260/619 |
| 4,912,263 | 3/1990 | Rudolph et al. | 568/722 |
| 4,982,014 | 1/1991 | Freitag et al. | 568/721 |
| 5,210,328 | 5/1993 | Freitag et al. | 568/721 |
| 5,212,206 | 5/1993 | Rudolph | 521/32 |
| 5,284,981 | 2/1994 | Rudolph et al. | 568/727 |

FOREIGN PATENT DOCUMENTS

| 481 287 | 10/1991 | European Pat. Off. |
|---|---|---|
| 36 19 450 A1 | 12/1987 | Germany . |
| 37 27 641 A1 | 3/1989 | Germany . |
| 4121791 | 1/1993 | Germany . |

OTHER PUBLICATIONS

Chemical Abstracts 58, 1403e.

*Primary Examiner*—Frederick Krass
*Attorney, Agent, or Firm*—Connolly and Hutz

[57] ABSTRACT

The invention relates to the synthesis of bisphenols from monophenols and carbonyl compounds such as aldehydes and ketones with concentrated mineral acids such as hydrochloric acid and/or hydrogen chloride gas as acid catalysts and a mercaptan as cocatalyst, which is fixed by an ion-pair bond to a matrix insoluble in the reaction medium.

3 Claims, No Drawings

PROCESS FOR THE PRODUCTION OF BISPHENOLS WITH THE USE OF NEW COCATALYSTS

The invention relates to the synthesis of bisphenols from monophenols and carbonyl compounds such as aldehydes and ketones with concentrated mineral acids such as hydrochloric acid and/or hydrogen chloride gas as acid catalysts and a mercaptan as cocatalyst, which is fixed by an ion-pair bond to a matrix insoluble in the reaction medium.

The condensation of phenols and carbonyl compounds for the formation of bisphenols with the use of catalysts such as hydrochloric acid (U.S. Pat. Nos. 2,182,308; 2,191,831) and also of sulphur-containing compounds as cocatalysts is known (e.g. from U.S. Pat. Nos. 2,468,982 and 2,623,908 the use of thioglycolic acid and 3-mercaptopropionic acid, from U.S. Pat. No. 2,775,620 the addition of alkylmercaptans, from Chemical Abstracts 58, 1403e the addition of hydrogen sulphide). In operating practice, the known sulphur-containing cocatalysts can lead to considerable discoloration of the bisphenols and of the subsequent products produced from them, as for example polycarbonates, copolycarbonates, polyesters, copolyesters and epoxy resins, if they are not removed without residue by appropriate purification measures, as for example crystallization of the bisphenol and washing-out of the sulphur compounds. The removal of the sulphur-containing components, especially in the case of bisphenols whose syntheses require very high concentrations of cocatalysts, is often difficult and coupled with undesirable losses of the required target compound, especially in the case of thermal stress, e.g. during the working-up.

On the other hand, cocatalysts can easily be removed completely by filtration or centrifugation if they are not charged in homogeneous phase but are already bound, before addition to the educt mixture, via ionic bonds to a matrix insoluble in the reaction medium. This form of the cocatalysts enables extremely high cocatalyst concentrations to be used without the quality problems described above occurring.

The synthesis of bisphenols with cocatalysts fixed to a resin matrix is described in DE-A 3 619 450 (e.g. with aminoalkylmercaptan units), or in DE-A 3 727 641 (e.g. with thiazolidine units), in which the catalyst acid which likewise is necessary is also bound to the resin matrix in the form of sulphonic acid groups.

These processes are not, however, equally suitable for the production of all bisphenols. Bisphenols from ketones with relatively high alkyl groups, such as dihydroxydiphenylcycloalkanes of the 1,1-bis(4-hydroxyphenyl)-3,3,5-trimethyl-cyclohexane type can be obtained in this way only with relatively low conversions of the appropriate ketone and low selectivity relating to undesired by-products. It has now been found that bisphenols of formula (I), as for example 1,1-bis(4-hydroxyphenyl)-3,3,5-trimethylcyclohexane, can be produced without problems with high ketone conversions and high selectivities with concentrated mineral acids such as hydrochloric acid and/or hydrogen chloride gas together with a sulphonic acid ion-exchanger resin based on a cross-linked polystyrene resin matrix, whose sulphonic acid groups have been partially, preferably completely, neutralized with an aminomercaptan and/or a thiazolidine, the complete conversion of the ketone being reached after shorter reaction times than is the case with the corresponding cocatalysts used in the homogeneous phase, such as mercaptans.

The present invention accordingly provides a process for the production of bisphenols of formula (I) by reaction of phenols of formula (V) and ketones of formula (VI).

Bisphenols of formula (I)

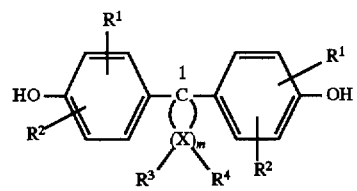

are those in which $R^1$ and $R^2$ independently of each other represent hydrogen, halogen, preferably chlorine or bromine, $C_1$–$C_8$ alkyl, $C_5$–$C_6$ cycloalkyl, $C_6$–$C_{10}$ aryl, preferably phenyl, and $C_7$–$C_{12}$ aralkyl, preferably phenyl-$C_1$–$C_4$-alkyl, in particular benzyl, m represents an integer from 4 to 7, preferably 4 or 5, $R^3$ and $R^4$, which can be selected individually for each X, represent, independently of each other, hydrogen or $C_1$–$C_6$ alkyl and X represents carbon, provided that on at least one atom X, $R^3$ and $R^4$ simultaneously represent alkyl; preferably on 1 to 2 atoms X, in particular on only one atom X, $R^3$ and $R^4$ are simultaneously alkyl.

The preferred alkyl group is methyl; the X atoms in the α position to the di-phenyl-substituted C atom (C–1) are preferably not dialkyl-substituted, but in the β position to C–1, on the other hand, alkyl disubstitution is preferred. The invention provides in particular dihydroxydiphenylcycloalkanes with 5 and 6 ring C atoms in the cycloaliphatic group (m=4 or 5) in formula (I), as for example the diphenols of the formulae

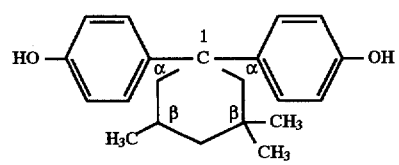

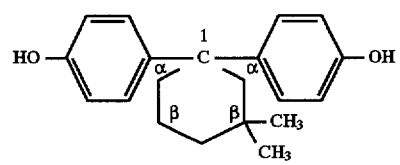

and

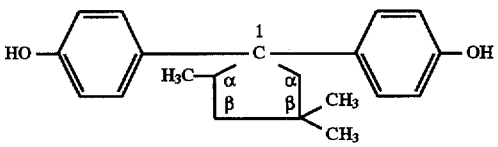

1,1-bis(4-hydroxyphenyl)-3,3,5-trimethylcyclohexane (formula (III)) being particularly preferred.

Phenols of formula (V)

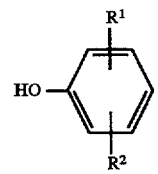

are those in which $R^1$ has the same meaning as in formula (I).

The phenols of formula (V) are either known in the literature or obtainable by methods known in the literature (see for example for cresols and xylenols, Ullmann's Encyclopedia of Industrial Chemistry, 4th, revised and enlarged ed., Vol. 15, pp 61 to 77, Verlag Chemie Weinheim-New York 1978; for chlorophenols, Ullmann's Encyclopedia of Industrial Chemistry, 4th ed., Verlag Chemie, 1975, Vol. 9, pp 573 to 582; and for alkylphenols, Ullmann's Encyclopedia of Industrial Chemistry, 4th Edition, Verlag Chemie 1979, Vol. 18, pp 191 to 214).

Examples of suitable phenols of formula (V) are: phenol, o-cresol, m-cresol, 2,6-dimethylphenol, 2-chlorophenol, 3-chlorophenol, 2,6-dichlorophenol, 2-cyclohexylphenol, diphenylphenol and o- and p-benzylphenols.

Ketones of formula (VI)

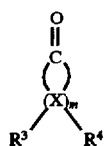

(VI)

are those in which X, $R^1$, $R^4$ and m have the same meanings as in formula (I).

Examples of known ketones of formula (VI) are: 3,3-dimethylcyclopentanone, 2,2-dimethylcyclohexanone, 3,3-dimethyl-cyclohexanone, 4,4-dimethylcyclohexanone, 3-ethyl-3-methylcyclopentanone, 2,3,3-trimethylcyclopentanone, 2,4,4-trimethylcyclopentanone, 3,3,4-trimethyl-cyclopentanone, 3,3-dimethylcycloheptanone, 4,4-dimethylcycloheptanone, 3-ethyl-3-methylcyclohexanone, 4-ethyl-4-methylcyclohexanone, 2,3,3-trimethyl-cyclohexanone, 2,4,4-trimethylcyclohexanone, 3,3,4-trimethylcyclohexanone, 2,5,5-trimethylcyclohexanone, 3,3,5-trimethylcyclohexanone, 3,4,4-trimethylcyclohexanone, 2,3,3,4-tetramethylcyclopentanone, 2,3,4,4-tetramethylcyclopentanone, 3,3,4,4-tetramethylcyclopentanone, 2,2,5-trimethylcycloheptanone, 2,2,6-trimethylcycloheptanone, 2,6,6-trimethylcycloheptanone, 3,3,5-trimethylcycloheptanone, 3,5,5-trimethylcycloheptanone, 5-ethyl-2,5-dimethylcycloheptanone, 2,3,3,5-tetramethylcycloheptanone, 2,3,5,5-tetramethylcycloheptanone, 3,3,5,5-tetramethylcycloheptanone, 4-ethyl-2,3,4-trimethylcyclopentanone, 2-isopropyl-4,4-dimethylcyclopentanone, 4-isopropyl-2,4-dimethylcyclopentanone, 2-ethyl-3,5,5-trimethylcyclohexanone, 3-ethyl-3,5,5-trimethylcyclohexanone, 3-ethyl-4-isopropyl-3-methylcyclopentanone, 4-sec-butyl-3,3-dimethylcyclopentanone, 2-isopropyl-3,3,4-trimethylcyclopentanone, 3-ethyl-4-isopropyl-3-methylcyclohexanone, 4-ethyl-3-isopropyl-4-methylcyclohexanone, 3-sec-butyl-4,4-dimethylcyclohexanone, 3-isopropyl-3,5,5-trimethylcyclohexanone, 4-isopropyl-3,5,5-trimethylcyclohexanone, 3,3,5-trimethyl-5-propylcyclohexanone, 3,5,5-trimethyl-5-propylcyclohexanone, 2-butyl-3,3,4-trimethylcyclopentanone, 2-butyl-3,3,4-trimethylcyclohexanone, 4-butyl-3,3,5-trimethylcyclohexanone, 3-isohexyl-3-methylcyclohexanone, 5-ethyl-2,4-diisopropyl-5-methylcyclohexanone, 2,2-dimethylcyclooctanone and 3,3,8-trimethyl-cyclooctanone.

Examples of preferred ketones are

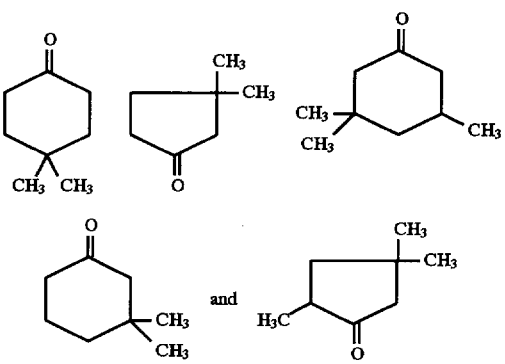

The ketones of formula (VI) are known in the literature (see for example) Beilsteins Handbuch der Organischen Chemie, Vol. 7, 4th ed., Springer Verlag, Berlin, 1925, and the corresponding Supplementary Vols. 1 to 4 and J. Am. Chem. Soc. Vol. 79 (1957), pp. 1488, 1490 and 1491, U.S. Pat. No. 2,692,289, Allen et at., J. Chem. Soc., (1954), 2186, 2191 and J. Org. Chem. Vol. 38, No. 26 (1973), pp. 4431 ff, J. Am. Chem. Soc. 87 (1965), pp. 1353 ff, especially p. 1355. A general process for the production of ketones of formula (VI) is described for example in "Organikum", 15th ed., 1977, VEB-Deutscher Verlag der Wissenschaften, Berlin, e.g. p. 698.

The process is characterized in that a mineral acid, preferably hydrochloric acid, and/or HCl gas, is added as catalyst to a mixture of a phenol of formula (V), a ketone of formula (VI) and a sulphonic acid ion-exchanger resin based on a cross-linked polystyrene resin matrix whose sulphonic acid groups have been at least 10%, preferably completely, neutralized by means of a mercaptoamine and/or a thiazolidine, the reaction temperatures being maintained between 20 ° C. and 90 ° C., preferably between 25 ° C. and 40 ° C. The acid ion-exchanger resin is subsequently removed by filtering off at 65 ° C. to 90 ° C., after the hydrochloric acid and/or the HCl gas has been removed, preferably by reduction of the pressure at temperatures between 30 ° C. and 70 ° C. The product is then purified according to the conventional methods by recrystallization in phenol, phenol and water or other suitable organic solvents.

A mixture of 36% hydrochloric acid and HCl gas is preferably used as mineral acid. In doing so, 1 kg 36% hydrochloric acid and 1 kg HCl gas are used per 18 to 180 tool of the ketone of formula (I). Most preferably HCl gas is used without hydrochloric acid, the concentration of the HCl gas in the reaction mixture in this case being between 0.5 wt. % and 5.0 wt. %, preferably between 1.0 wt. % and 2.0 wt. %, based on the whole reaction mixture, including the HCl gas.

A sulphonated ion-exchanger resin based on a cross-linked polystyrene is used as cocatalyst, the acid groups of the ion-exchanger resin having been at least 10%, but preferably completely, neutralized by mercaptoamines or thiazolidines before charging to the reaction mixture and the amount used of the cocatalyst according to the invention being selected so that the molar ratio of mercapto groups to ketone amounts to at least 1:10, preferably 1:1 to 10:1.

Before use in the bisphenol synthesis, the acid ion-exchanger resin is washed with distilled or demineralized water until the wash water has a conductivity of less than 100 µS. The water is subsequently removed from the ion exchanger resin by drying in conventional drying units or displacement by anhydrous phenol. Finally, the ion-exchanger resin is partially or completely neutralized in phenolic suspension of the ion-exchanger resin with a mercaptoamine and/or a thiazolidine.

The degree of cross-linking of these polystyrenes can be between 0.5% and 50%, preferably between 1% and 8%, in which the degree of cross-linking means the amount used of comonomer with cross-linking activity in mol %, based on the moles of styrene used during the copolymerization.

The mercaptans are preferably ω-aminoalkylmercaptans; 2,2-dimethylthiazolidine is preferably suitable as a thiazolidine.

The bisphenols produced according to the present invention are particularly suitable for the synthesis of polycarbonates, copolycarbonates, polyesters, copolyesters and epoxy resins.

EXAMPLES

A. Preparation of the Ion-exchanger Resin as Cocatalyst for the Bisphenol Synthesis 300 g water-wet, acid ion-exchanger resin (Lewatit SC 102, Bayer AG) are washed with completely demineralized water until the wash water has a conductivity of less than 100 μS. Subsequently, the Lewatit is filtered vigorously by suction over a vacuum nutsche and dried in the vacuum drying oven for 72 hours at 100° C. and 20 mbar. The substance weighed after drying shows about 60 g dry Lewatit SC 102.

60 g dry ion-exchanger resin Lewatit SC 102 are stirred for 4 hours in 300 ml phenol (water content <0.1%) in order that it shall be able to swell completely. Subsequently 26.5 g 2,2-dimethylthiazolidine in 100 ml phenol are added and the mixture stirred at 65° C. for 24 hours in a round-bottomed flask. Thereafter the resin is filtered off and vigorously sucked off and the bisphenol A formed and unbound dimethylthiazolidine are rinsed out with fresh phenol until bisphenol A and dimethylthiazolidine can no longer be detected in the eluate.

B. Synthesis of TMC-BP

Example 1 with concentrated hydrochloric acid and HCl gas:

In a stirring apparatus, HCl gas is introduced at 30° C. for 1 hour into a mixture of 499 g phenol, 64 g 3,3,5-trimethylcyclohexanone, 3.74g 36% hydrochloric acid and 125 g of the ion-exchanger resin prepared according to A. Stirring is continued for a further 9 hours and the ketone conversion and selectivity of the reaction are then determined.
Ketone conversion: 97 to 99%
Selectivity: 85 % 1,1-bis(4-hydroxyphenyl)-3,3,5-trimethylcyclohexane Example 2 with HCl gas only:

In a stirring apparatus, HCl gas is introduced at 30° C. for 1 hour into a mixture of 499 g phenol, 64 g 3,3,5-trimethylcyclohexanone and 125 g of the ion-exchanger resin prepared according to A. Stirring is continued for a further 9 hours and the ketone conversion and selectivity of the reaction are then determined.
Ketone conversion: 97 to 99%
Selectivity: 90% 1,1-bis(4-hydroxyphenyl)-3,3,5-trimethylcyclohexane Example 3 (Comparative example corresponding to the conventional production process)

In a stirring apparatus, HCl gas is introduced at 30° C. for 1 hour into a mixture of 499 g phenol, 64 g 3,3,5-trimethylcyclohexanone, 3.74 g 36% hydrochloric acid and 0.19. g methyl 3-mercaptopropionate. Stirring is continued for a further 19 hours and the ketone conversion and selectivity of the reaction are then determined.
Ketone conversion after 20 hours: 100%
Selectivity: 81% 1,1-bis(4-hydroxyphenyl)-3,3,5-trimethylcyclohexane

We claim:
1. Process for the production of bisphenols of the formula

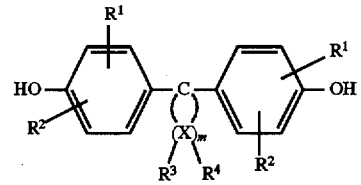

by reaction of phenols of the formula

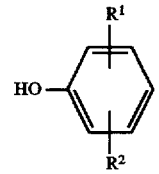

and ketones of the formula

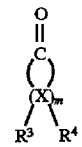

in which
$R^1$ and $R^2$ independently of each other represent hydrogen, halogen, $C_1$–$C_8$ alkyl, $C_5$–$C_6$ cycloalkyl, $C_6$–$C_{10}$ aryl or $C_7$–$C_{12}$ aralkyl,
m represents an integer from 4 to 7,
$R^3$ and $R^4$, which can be selected individually for each X, represent, independently of each other, hydrogen or $C_1$–$C_6$ alkyl and
X represents carbon,
provided that on at least one atom X, $R^3$ and $R^4$ simultaneously represent alkyl,
wherein a mineral acid and/or HCl gas is used as catalyst and a sulphonic acid ion-exchanger resin based on a cross-linked polystyrene as cocatalyst, in which the acid groups of the ion-exchanger resin have been at least 10% neutralized by mercaptoamines and/or thiazolidines before charging to the reaction mixture and the amount of the cocatalyst used is selected so that the molar ratio of mercapto groups and ketone used is at least 1:10.

2. Process according to claim 1, wherein the acid ion-exchanger resin before use in the bisphenol synthesis is washed with distilled or demineralized water until the wash water has a conductivity of less than 100 μS, the water is subsequently removed from the ion exchanger resin by drying in drying units or by displacement by anhydrous phenol and finally the ion-exchanger resin is partially or completely neutralized in phenolic suspension with a mercaptoamine and/or a thiazolidine.

3. Process according to claim 1, characterized in that after the end of the reaction, the ion-exchanger resin is separated off from the reaction products by filtering off or by centrifuge, after the acid and/or the HCl gas have been removed from the reaction mixture.

* * * * *